(12) United States Patent
Harada et al.

(10) Patent No.: US 6,821,446 B2
(45) Date of Patent: Nov. 23, 2004

(54) REMOVAL METHOD FOR COATING OF POLYMER COATED GLASS CAPILLARY TUBING AND POLYMER COATED GLASS CAPILLARY TUBING

(75) Inventors: Kunio Harada, Hachioji (JP); Masao Kamahori, Kokubunji (JP); Hideki Kambara, Hachioji (JP); Sumio Yamaguchi, Hamura (JP); Sukeyoshi Tsunekawa, Iruma (JP)

(73) Assignee: Hitachi, Ltd., Tokyo (JP)

( * ) Notice: Subject to any disclaimer, the term of this patent is extended or adjusted under 35 U.S.C. 154(b) by 44 days.

(21) Appl. No.: 09/944,410

(22) Filed: Sep. 4, 2001

(65) Prior Publication Data

US 2002/0028308 A1 Mar. 7, 2002

(30) Foreign Application Priority Data

Sep. 5, 2000 (JP) ........................................ 2000-269218

(51) Int. Cl.$^7$ ............................................... C03C 15/00
(52) U.S. Cl. ................................ 216/8; 216/24; 216/55; 216/66; 216/67; 264/446; 264/347
(58) Field of Search ............................. 216/8, 24, 55, 216/66, 67; 134/1.1, 25.1, 19; 510/201; 264/446, 447

(56) References Cited

U.S. PATENT DOCUMENTS

| | | | | |
|---|---|---|---|---|
| 4,902,323 A | * | 2/1990 | Miller et al. | 65/407 |
| 4,940,883 A | | 7/1990 | Karger et al. | 219/200 |
| 5,762,755 A | * | 6/1998 | McNeilly et al. | 438/708 |
| 5,994,232 A | * | 11/1999 | Clampitt | 438/706 |
| 6,184,119 B1 | * | 2/2001 | Ku et al. | 438/597 |
| 6,242,165 B1 | * | 6/2001 | Vaartstra | 430/329 |
| 6,413,827 B2 | * | 7/2002 | Farrar | 438/296 |

FOREIGN PATENT DOCUMENTS

| | | | | | |
|---|---|---|---|---|---|
| JP | 60143827 A | * | 7/1985 | ............ | B01J/19/12 |
| JP | 01025866 A | * | 1/1989 | ............ | A61L/02/20 |
| JP | 05-232085 | | 2/1992 | | |
| JP | 06-074938 | | 8/1992 | | |
| JP | 10-206383 | | 1/1997 | | |
| JP | 11-230939 | | 2/1998 | | |

* cited by examiner

Primary Examiner—Allan Olsen
(74) Attorney, Agent, or Firm—Reed Smith LLP; Stanley P. Fisher, Esq.; Juan Carlos A. Marquez, Esq.

(57) ABSTRACT

The present invention provides a method for producing a high-quality capillary tube used in an electrophoresis apparatus in a safe and inexpensive manner. A polymer coating on a capillary tube is converted into gas and removed through an oxidative reaction with oxygen radicals resulting from ozone decomposition.

11 Claims, 14 Drawing Sheets

MAGNIFIED OF A (BY THIS INVENTION)

MAGNIFIED OF A (BY THE TECHNOLOGY IN THE PAST)

US 6,821,446 B2

REMOVAL METHOD FOR COATING OF POLYMER COATED GLASS CAPILLARY TUBING AND POLYMER COATED GLASS CAPILLARY TUBING

FIELD OF THE INVENTION

The present invention relates to a polymer-coated capillary tube used in an electrophoresis apparatus, to a method for processing a window at a predetermined position of the capillary tube for enhancing a light transmittance thereof and to a capillary tube whose coating is selectively removed to provide a window by the method.

BACKGROUND ART

Electrophoresis apparatuses that utilize capillary tubes for rapid processing of mass data are widely used in DNA nucleotide sequence analyses. The capillary tubes used are generally glass tubes having an inner diameter of 1 to 800 μm, an outer diameter of 50 to 1,000 μm and a length of 50 to 2,000 mm, which is coated with a polymer to a thickness of 10 to 30 μm, among which a capillary tube of an appropriate size is employed. Polymer, generally polyimide, is coated to enhance the mechanical strength and give flexibility to the fragile glass tube for easy handling. However, since a sample migrating inside a capillary tube is detected by irradiating the fluorescence-labeled sample with a laser beam from outside the capillary tube and detecting the excited fluorescence, a polymer coating with a poor light transmittance will interfere with the sample detection. Thus, it is necessary to selectively remove the polymer coating for a length of about 1 to 20 mm around the periphery of the capillary tube. The portion removed of the polymer coating for an increased light transmittance is generally called a "window".

In order to process a window for a capillary tube, a technique in which a polymer coating is removed by burning with a lighter flame is generally employed when the number of capillary tubes is small. When the number of the capillary tubes is large, a technique such as one disclosed in JP-A-5-232085 may be employed in which a plurality of capillary tubes are supported at the same time to burn and remove predetermined regions of the polymer coating with a gas burner. However, burning with a lighter or a gas burner will leave cinders on the surfaces of the capillary tubes, and thus requires an after-treatment for wiping the cinders away with a wiper such as paper or cloth, which causes an increase in the production cost. Furthermore, wiping with the wiper may damage the exposed glass tube region. If the exposed glass tube region has a damage, the capillary tube can be susceptible to breakage during operations such as mounting the capillary tube on an apparatus. In addition, controlling the temperature of the flame is difficult since burning at a low temperature will leave a large amount of cinders and burning at a high temperature will result in deformation or poor transmittance of the glass capillary tube. Cinders on the window will interfere with the detection of fluorescence excited by laser irradiation.

In order to process a window by burning the polymer coating under a controlled temperature, techniques using an electric heater as disclosed in U.S. Pat. No. 4,940,883 (1990), JP-A-10-206383, JP-A-11-230939 may be employed. However, even under a controlled temperature, polymer coating is difficult to be burnt completely at or below an allowable continuous temperature of synthesized quartz (about 950° C.) that is generally used for making the glass tube, and a border between regions heated and unheated by the electric heater always includes insufficiently heated parts. As a result, after-treatment for wiping away the cinders is inevitable. Even if the window is elegantly processed, remaining cinders may fall off after the capillary tube is mounted on the electrophoresis apparatus, and may stick to a part that may cause an adverse effect on detection.

As a processing technique other than burning, JP-A-6-74938 discloses a technique for mechanically removing the coating with a scraper. However, it is difficult to remove the coating efficiently without damaging the glass tube. According to another technique, the polymer coating, will be sublimed through ablation with an excimer laser. However, this technique requires an expensive device and a large installation area. Compounds such as hot sulfuric acid and hydrazine may be used for removing the coating. However, they are hazardous and thus have drawbacks such as difficult handling, requirement of after-treatment, requirement of waste fluid processing and a risk of causing adverse effects on the environment.

A capillary tube provided with a window is susceptible to breakage because stresses caused upon bending or pulling the capillary tube may concentrate on the damage of the exposed glass region. The polymer coating is provided basically to enhance the mechanical strength and flexibility of the glass tube. Another reason for easy breakage of the capillary tube by the concentration of the stresses on the exposed portion is the profile of the edge of the coating at the window. When the edge of the coating at the window is removed generally perpendicular to the longitudinal direction of the capillary tube, the stresses will be concentrated on the edge of the coating at the window upon bending the tube and cause easy breakage.

In a multi-capillary electrophoresis apparatus, a plurality of capillary tubes are used as a multi-capillary array with the windows arranged in parallel to form a plane with the ends of the tubes being aligned. The windows of the multi-capillary array are supported by a holder so that the tubes are held secure. Capillary tubes having windows are used to produce the multi-capillary array. Since the mechanical strength of the glass capillary tubes with exposed windows is poor, they are difficult to be handled upon assembly, which interferes with automation of producing a multi-capillary array.

The above-described conventional techniques have adverse effects on the strength and the measurement due to damage, deformation, poor transmittance or the like of a glass capillary tubes and have the following problems: requirement of an after-treatment following the coating removal; requirement of an expensive device and a large installation area for the device; or use of a compound that may be hazardous to humans and the environment. In addition, conventional techniques have a problem of being susceptible to breakage which is caused by concentration of stresses on the edge of the coating at the window of the capillary tube, and a problem of automation in assembling fragile capillary tubes having windows being impossible for producing a multi-capillary array.

The present invention has an objective of providing a tough capillary tube provided with a window, which is produced in a safe and inexpensive manner by a method that causes no adverse effect, such as damage, deformation, poor transmittance or the like on a glass tube as a main body of the capillary tube, which may interfere with optical detection of a sample by an electrophoresis apparatus and while saving trouble such as wiping after the coating removal. The present invention also has an objective of providing means for automating production of a multi-capillary array, which has been impossible.

SUMMARY OF THE INVENTION

The above-mentioned objectives are achieved by applying a reactive gas such as ozone to a selective region of a capillary tube where a window is to be processed. Specifically, according to the present invention, one or more capillary tubes are placed in a reaction chamber such that a desirable window-processing length of about 1 to 20 mm of the capillary tubes is exposed inside the space of the reaction chamber. Then, a reactive gas containing ozone is supplied to the space inside the reaction chamber. The parts of the capillary tubes in the space as well as the reactive gas are heated so that the ozone contained in the reactive gas is decomposed to generate oxygen radical. Only the polymer coating on the parts exposed to the space inside the reaction chamber will be converted into gas and removed through an oxidative reaction with the oxygen radical.

According to this method, windows can be processed by removing the polymer coating at a much lower temperature (400° C. or lower) than a heat deformation temperature of the capillary tubes. By heating as well as radiating ultraviolet ray to the capillary tubes and the reactive gas filling the space inside the reaction chamber, ozone will absorb the ultraviolet ray (254 nm) to be more susceptible to decomposition. Thus, the windows can be processed through polymer coating removal at a lower temperature (250° C. or lower). In order to remove only the coatings on the predetermined regions of the capillary tubes, the plurality of capillary tubes are arranged perpendicular to the flow of the reactive gas while only the window-processing parts are surrounded by the semi-sealed reactive unit. Since the capillary tubes are supported by a holder, windows can be processed without the risk of damaging the tubes.

As shown in FIGS. 3 to 6, the reaction chamber is a hollowed space formed between and at generally the center of two substrates sandwiching the capillary tubes. One of the two substrates is provided with one or more grooves for supporting the capillary tubes. The reaction chamber is provided with a supply port and a discharge port for the reactive gas, which are provided at opposite sides of and appropriately apart from the space of the reaction chamber. The reactive gas introduced from the supply port into the space of the reaction chamber flows across the surfaces of the capillary tubes in the reaction chamber and discharged from the discharge port.

The capillary tubes are heated through heat transfer by mounting the two substrates sandwiching the capillary tubes on a heating plate above the device body. The temperature of the capillary tubes is lower than the maximum heat resistant temperature of polyimide (material of the polymer coating). When the reactive gas makes contact with the heated capillary tubes, the temperature of the capillary tubes is decreased and the oxidative reaction is suppressed. Therefore, the reactive gas is pre-heated to achieve a temperature generally equal to the temperature of the capillary tubes immediately before the reactive gas makes contact with the capillary tubes, thereby shortening the time required for processing the windows. The reactive gas is pre-heated by providing a heater or the like at the pipe immediately in front of the reactive gas supply port, by extending the distance between the supply port and the capillary tubes so that the reactive gas is heated to a temperature generally equal to that of the capillary tubes by the heating unit for the capillary tubes, or by transferring the heat from the heating plate from the reactive gas supply port to a pipe extending to an ozone generator so that the reactive gas is pre-heated to a temperature generally equal to that of the capillary tubes while flowing through the pipe.

Removal of the polymer coating using the reactive gas containing ozone takes place by supplying ozone to the heated polymer coating, by which the ozone will make contact with the heated capillary tubes or the ozone will be pre-heated by the pre-heating mechanism to be decomposed into $O_2$ and O radical, thereby promoting the oxidative reaction. However, the coating is not removed when either heating or reactive gas supply is lacking. In order not to remove the polymer coating on the capillary tubes other than the parts in the reaction chamber, dimensional tolerances of the width and the depth of the grooves for supporting the capillary tubes are slightly larger than the size of the capillary tubes to allow a slight amount of gas to flow between the capillary tubes and the grooves supporting the capillary tubes. As a result, a slight amount of atmosphere will be drawn in the space inside the reaction chamber and the ozone will make contact with the capillary tubes only into the space inside the reaction chamber. This structure allows the length of the processed windows to be generally equal to the length of the parts of the capillary tubes exposed to the space inside the reaction chamber. Accordingly, the length of the windows to be processed can be adjusted by varying the size of the reaction chamber. Since a slight amount of atmosphere is drawn into the reaction chamber from the gap between the capillary tubes and the grooves, the ozone is supplied to the space inside the reaction chamber not by a pressure higher than the atmospheric pressure being applied to the supply port but by being drawn into the space through negative pressure by making the pressure at the discharge port lower than atmospheric pressure. This structure also serves as a seal to prevent the ozone from leaking outside the device.

By making the upper substrate of the two substrates sandwiching the capillary tubes from glass with a high light transmittance, the removal status of the polymer coating on the capillary tubes can be observed. Therefore, the termination of the window-processing operations can be determined or the capillary tubes can be heated with a lamp heater or a laser beam through the glass substrate. By radiating ultraviolet ray to the capillary tubes and the reactive gas filling inside the reaction chamber, the ozone will absorb the ultraviolet ray (254 nm) to be susceptible to decomposition, which allows removal of the polymer coating (window-processing) at a lower temperature (250° C. or lower).

The present invention applies the above-mentioned structures to produce a multi-capillary array in a simple manner. Specifically, the holder (made of non-polymer material in this case) for covering and holding parts of the multi-capillary array to prevent them from falling apart is used as a reaction chamber for processing the windows. According to this method, first, a multi-capillary array is assembled, and then they are provided with windows. Therefore, the multi-capillary array can be produced by using capillary tubes having no window, which are stronger and easier to handle, thereby greatly enhancing an operation efficiency. Furthermore, production of the multi-capillary array can be automated.

In order to remove the polymer coating on the capillary tubes, other than the reaction chamber, an ozone generator, an ozone killer for decomposing the remaining unreacted ozone, a power source, a controller and the like are necessary. These members can be connected via pipes or lines to be used in a window-processing device for capillary tubes. According to the present invention, each of the constituent members is optimized and accommodated in a single body to produce a device that is specialized in processing windows for capillary tubes, which can be used on a desk.

BRIEF DESCRIPTION OF THE DRAWINGS

FIG. 7 is a flowchart showing operations of the window-processing device for coated capillary tubes according to the present invention, after switching the power source on;

PREFERRED EMBODIMENTS OF THE INVENTION

Hereinafter, preferred embodiments of the present invention will be described in detail with reference to the accompanying drawings.

Figure 1:
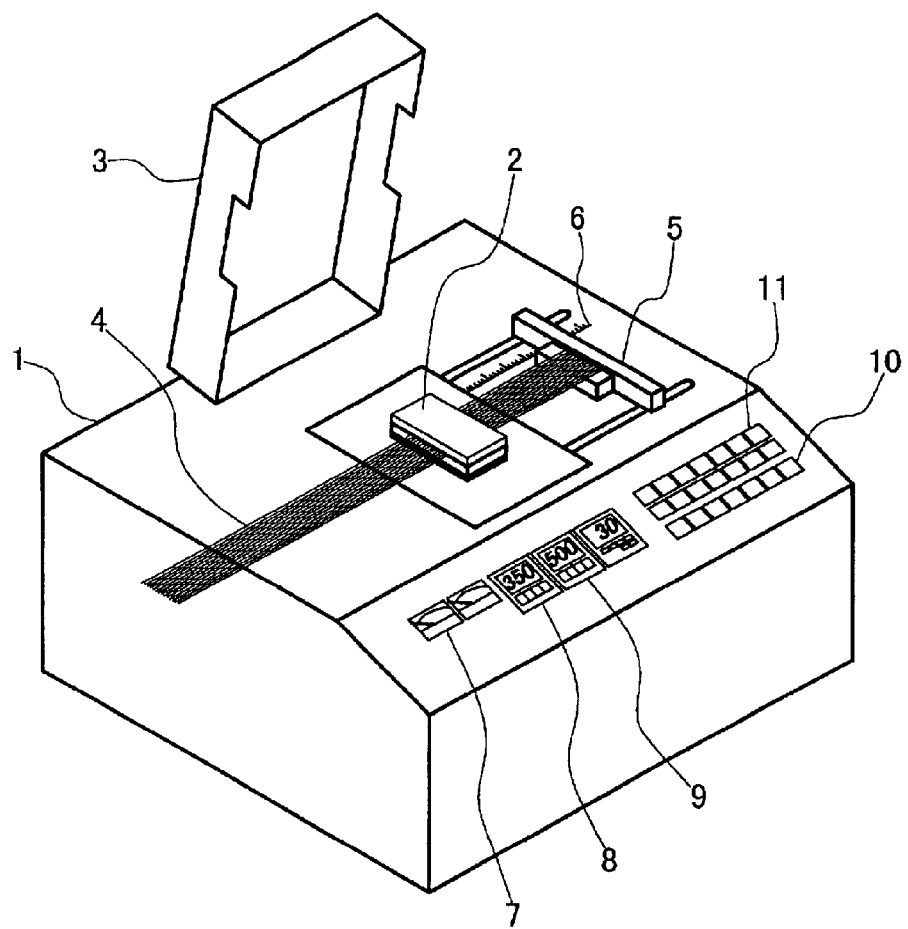
FIG. 1 is a perspective view showing a whole configuration of a window-processing device for coated capillary tubes according to the present invention.
Figure 2:
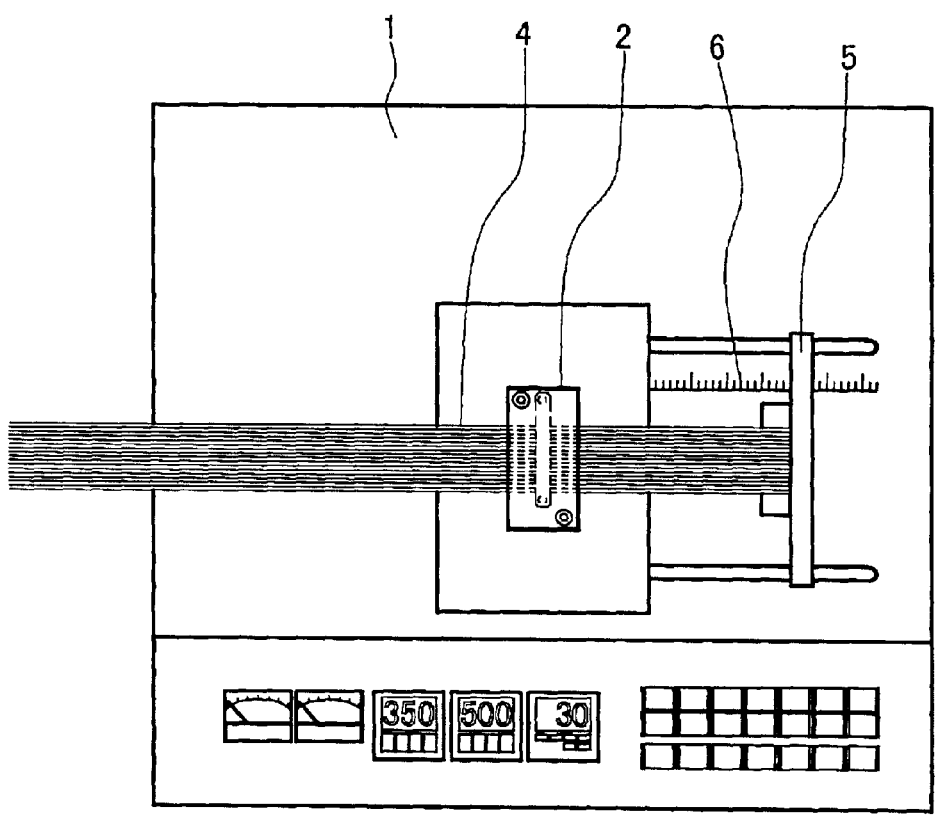
FIG. 2 is a plan view showing the whole configuration of the window-processing device for coated capillary tubes according to the present invention.
Figure 3:
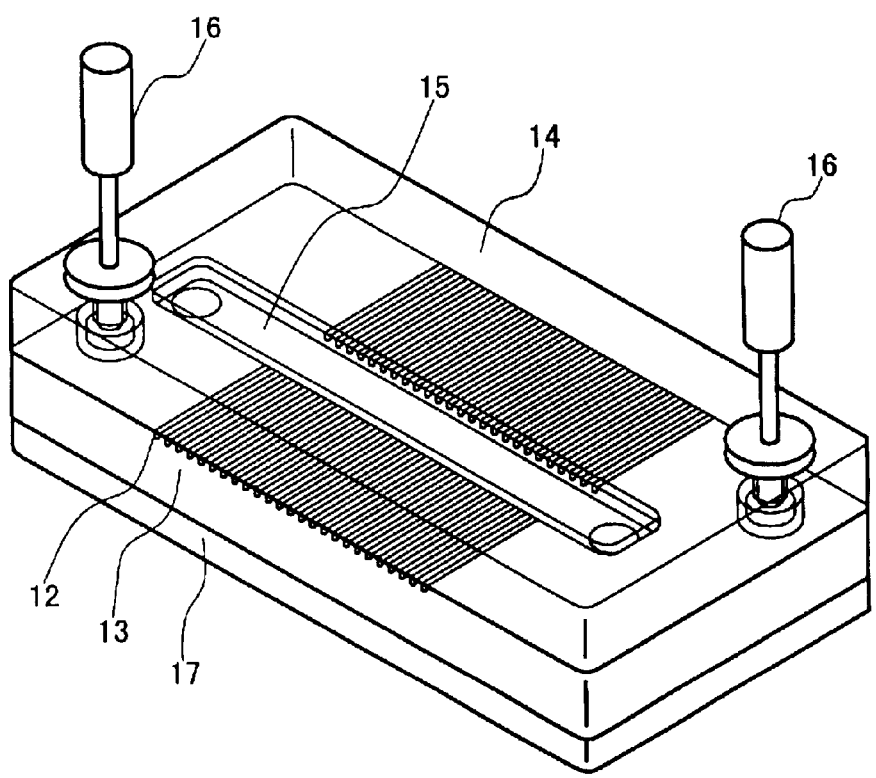
FIG. 3 is a perspective view of a reaction chamber and its periphery of the window-processing device for coated capillary tubes according to the present invention.
Figure 4:
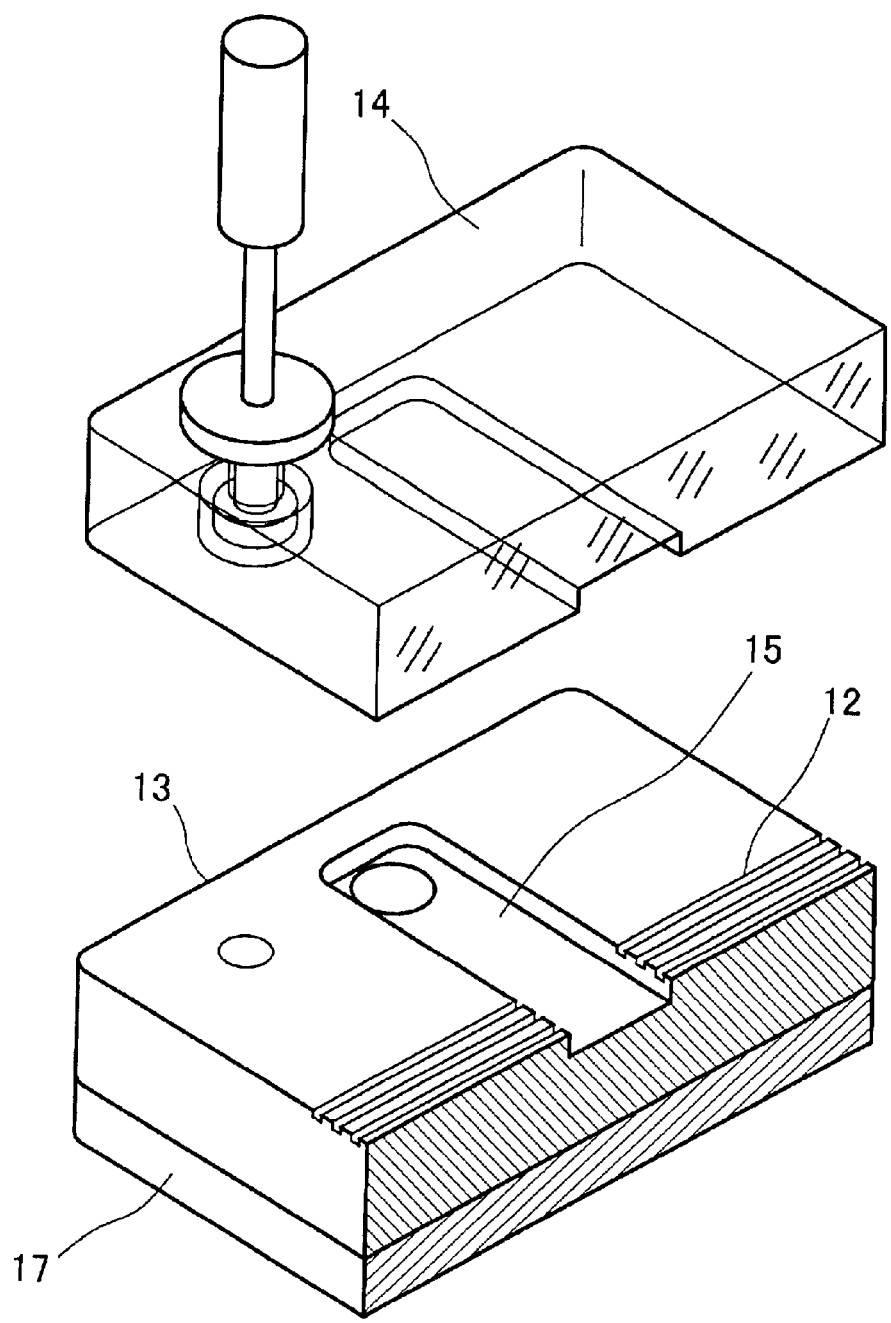
FIG. 4 is a magnified perspective view of the window-processing device for coated capillary tubes according to the present invention, including a cross-section of the reaction chamber.
Figure 5:
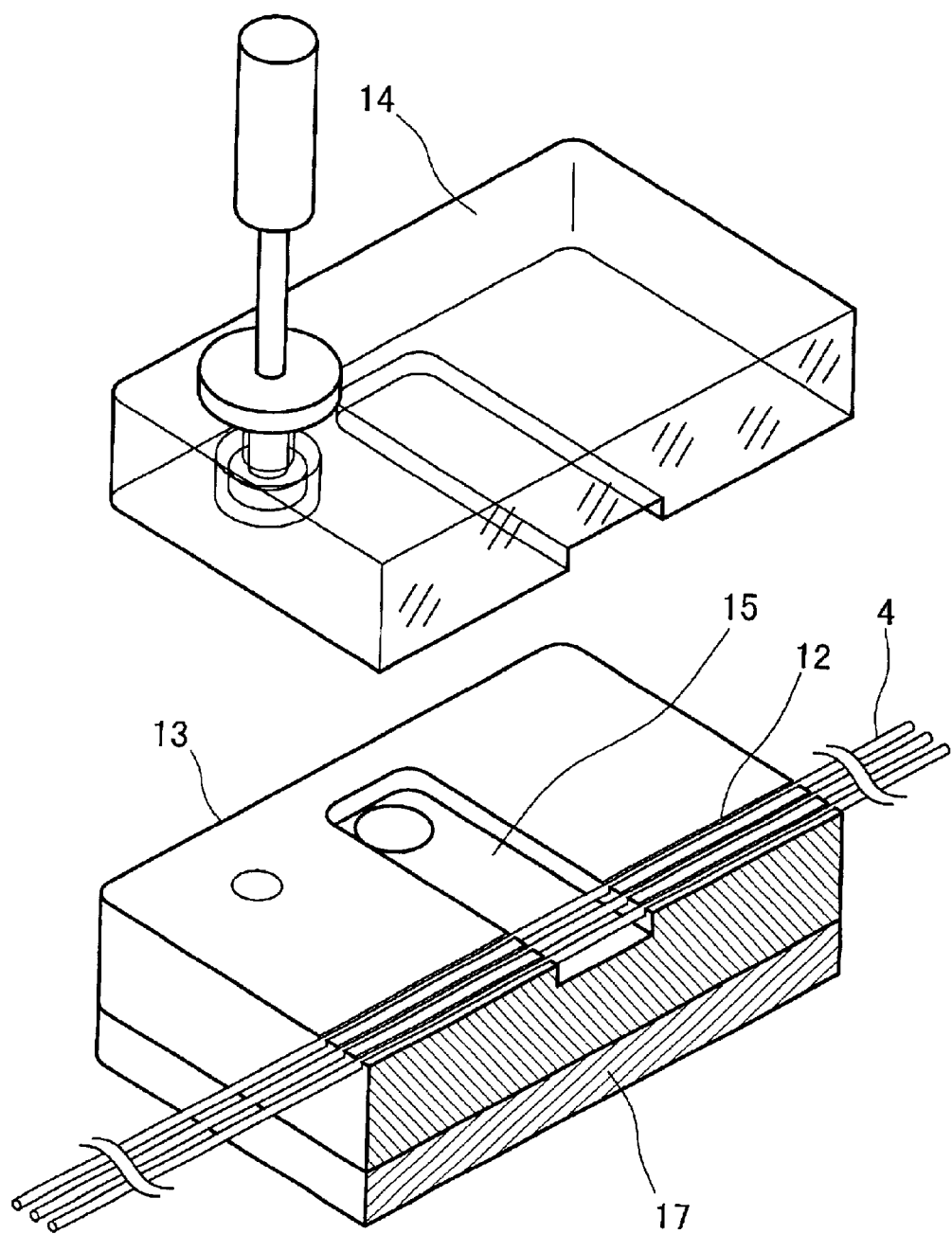
FIG. 5 is a magnified perspective view of the window-processing device for coated capillary tubes according to the present invention, including the cross-section of the reaction chamber.
Figure 6:
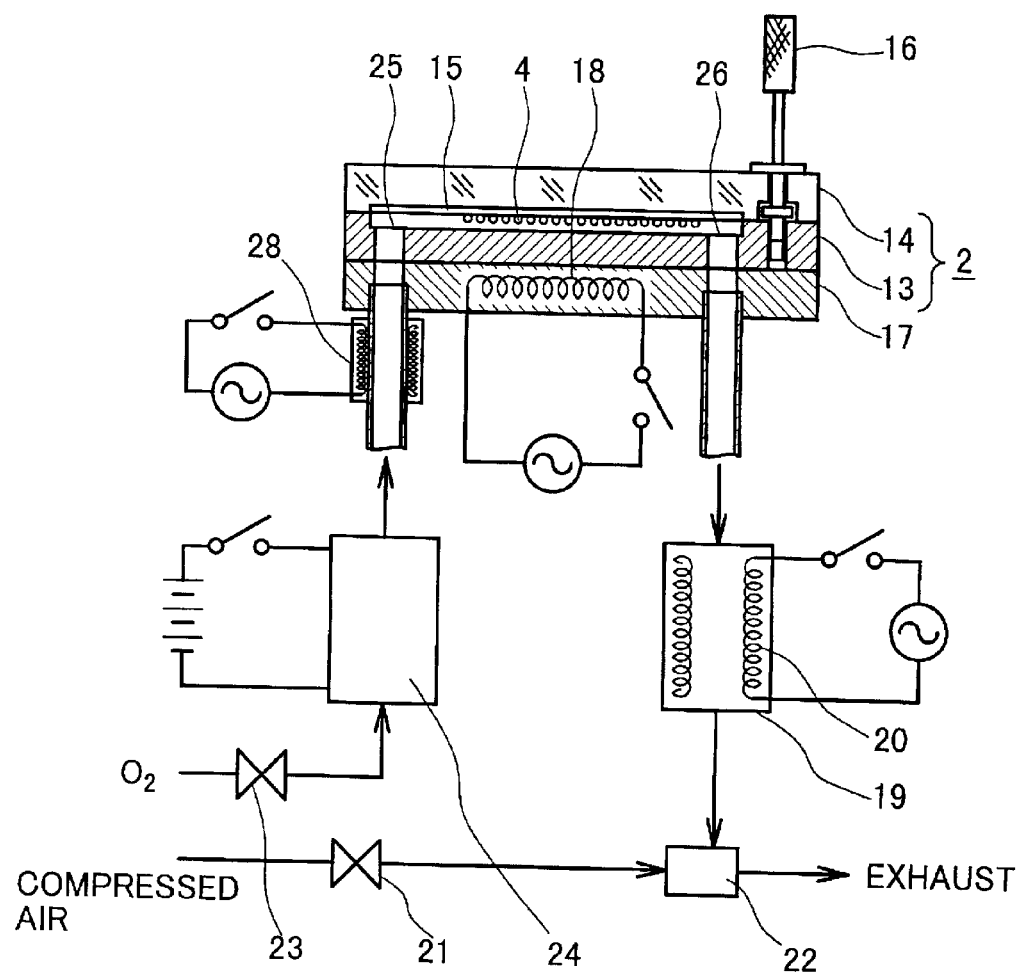
FIG. 6 is a cross-sectional view of the reaction chamber and a schematic piping diagram of the window-processing device for coated capillary tubes according to the present invention.
Figure 7:
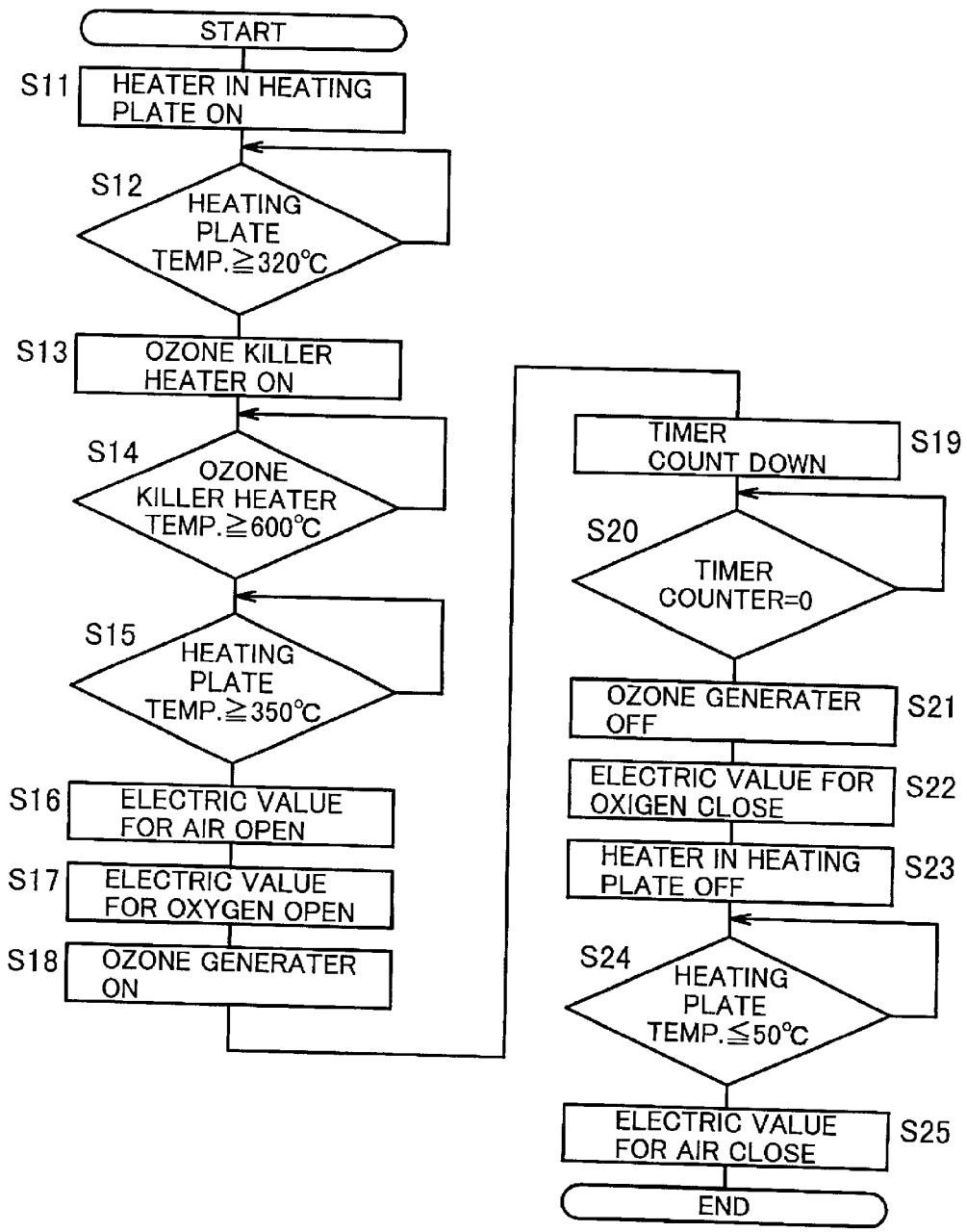
Figure 8:
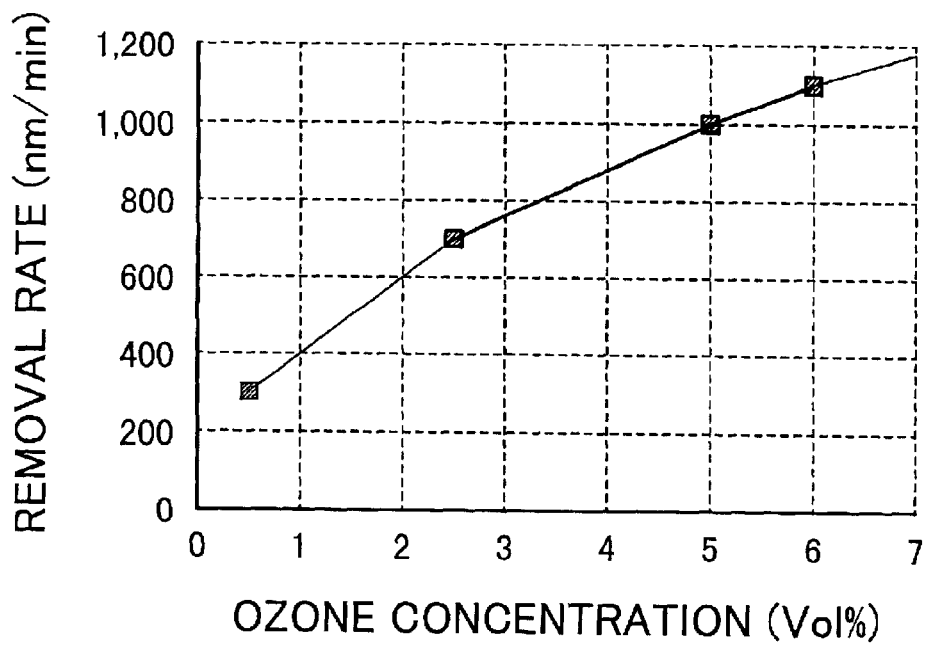
FIG. 8 is a graph showing relationship between ozone concentrations and removal rates.
Figure 9:
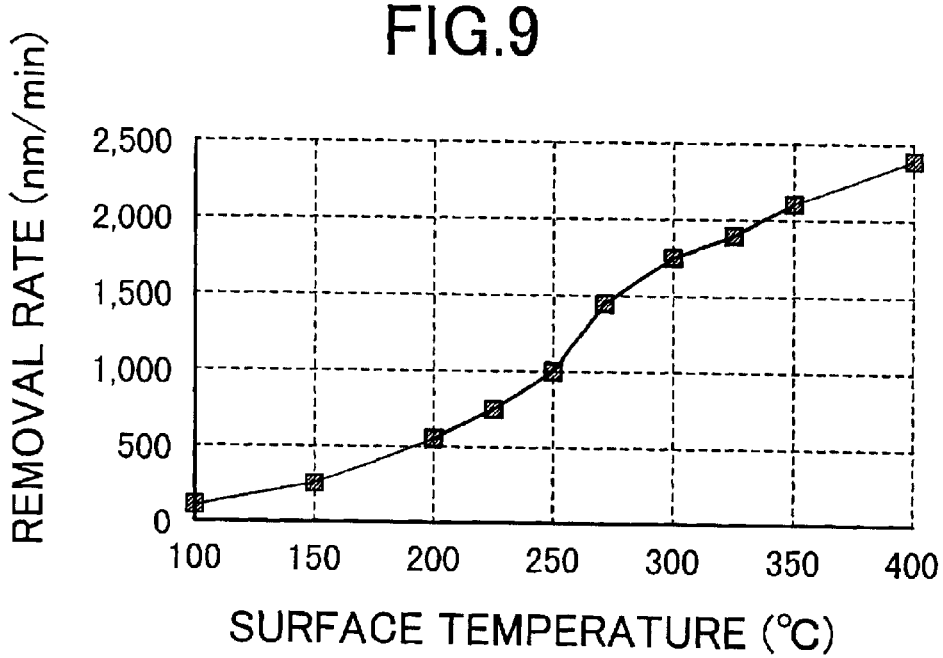
FIG. 9 is a graph showing relationship between window-processing temperatures and removal rates.
Figure 10A:
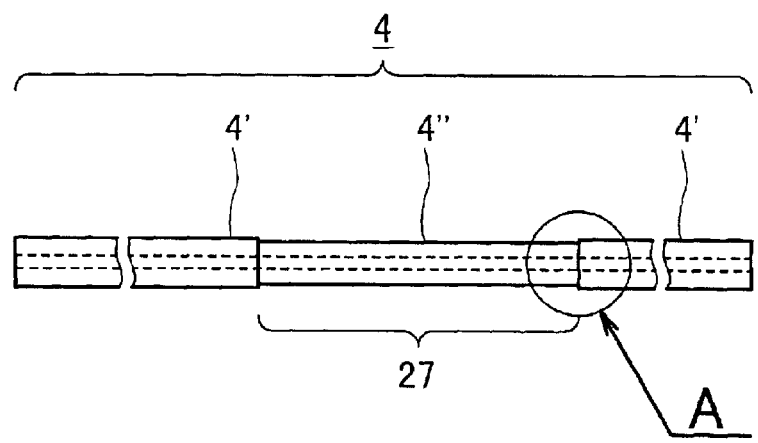
FIGS. 10A to 10C are magnified views of a processed window of a capillary tube.
Figure 10B:
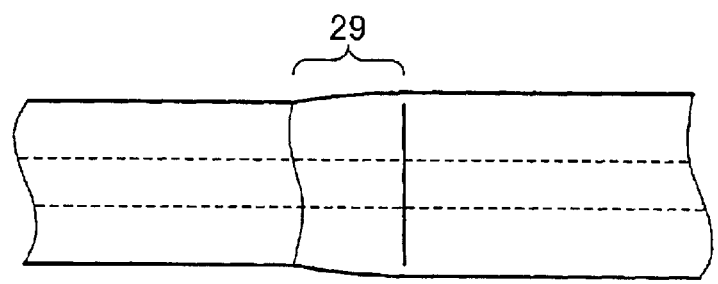
Figure 10C:
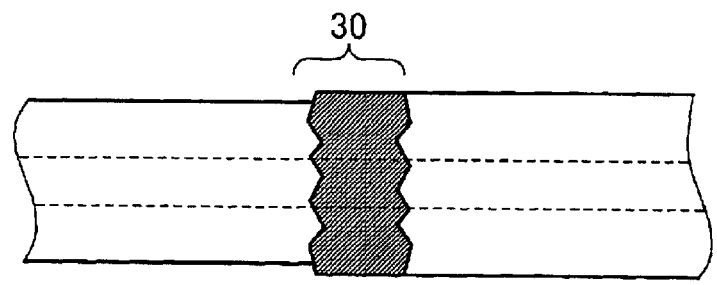
Figure 11A:
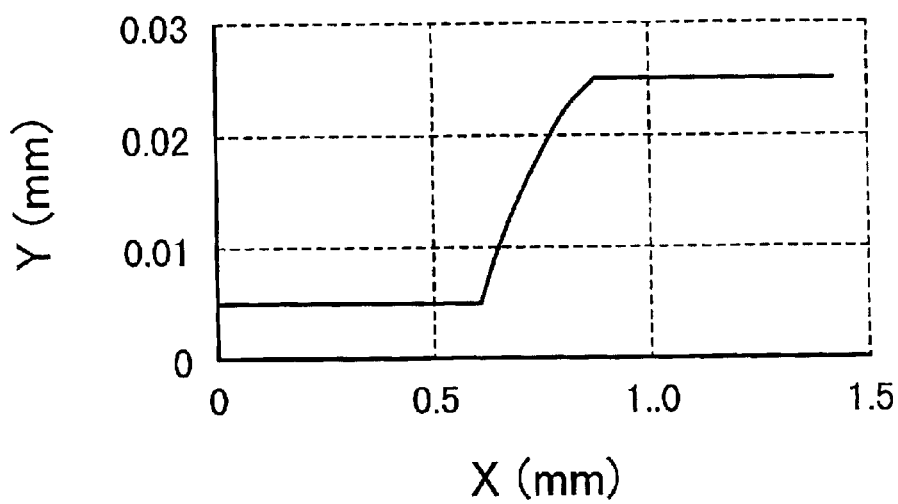
FIGS. 11A and 11B are graphs showing profiles of the surfaces of the processed windows of the capillary tubes.
Figure 11B:
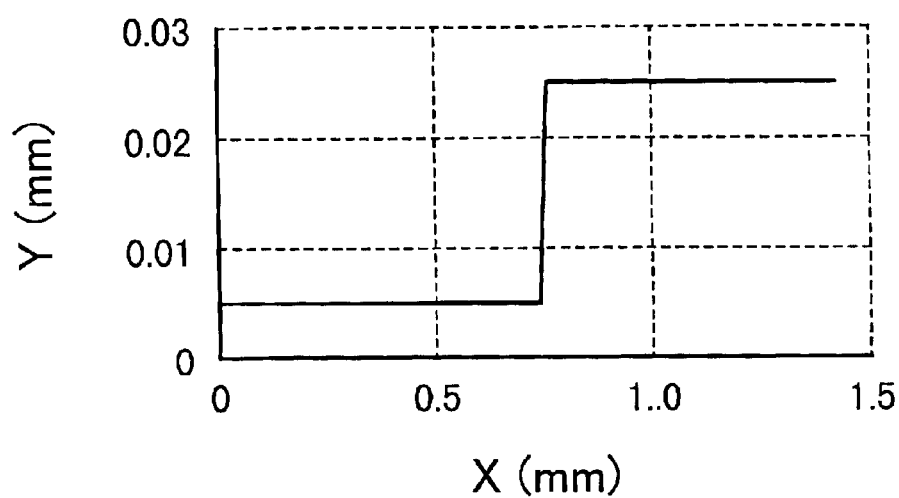
Figure 12:
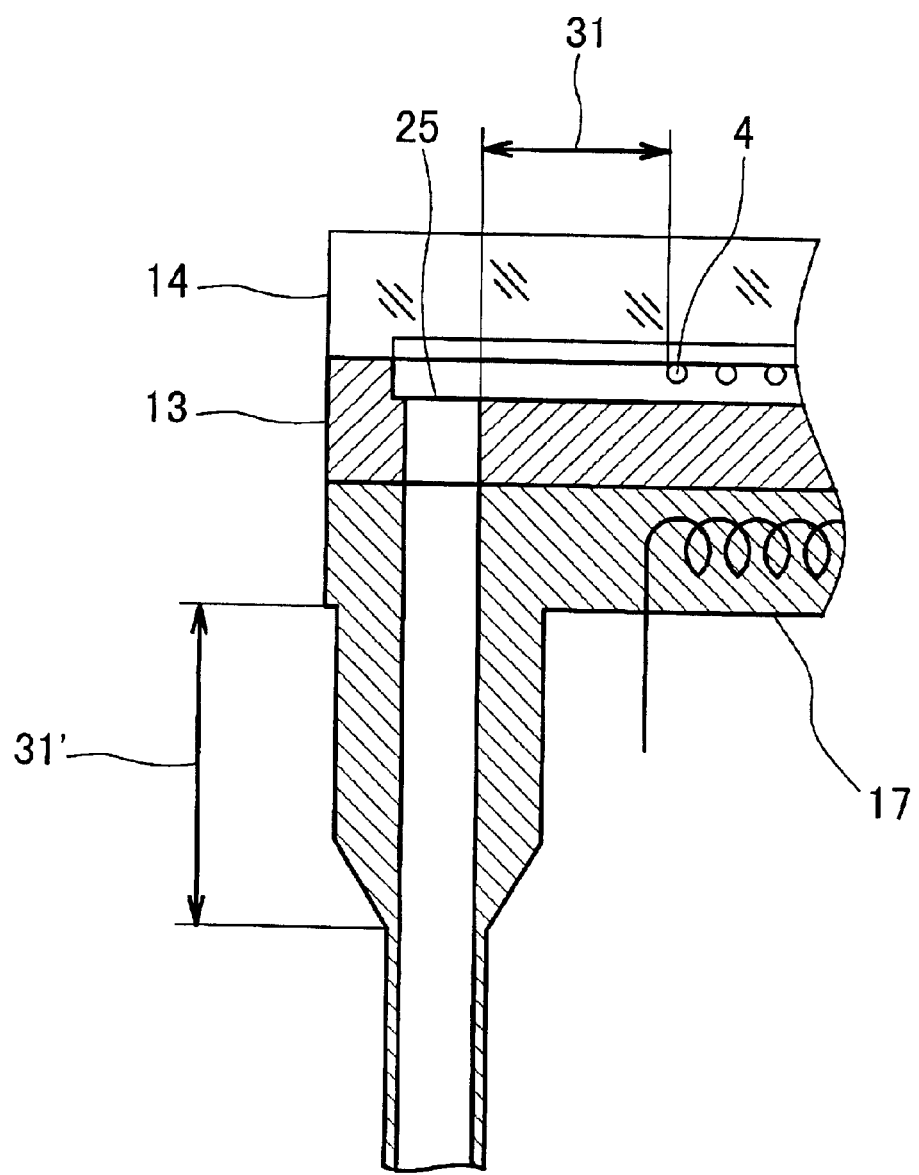
FIG. 12 is a partial magnified view of the reaction chamber of the window-processing device for coated capillary tubes according to the present invention.
Figure 13:
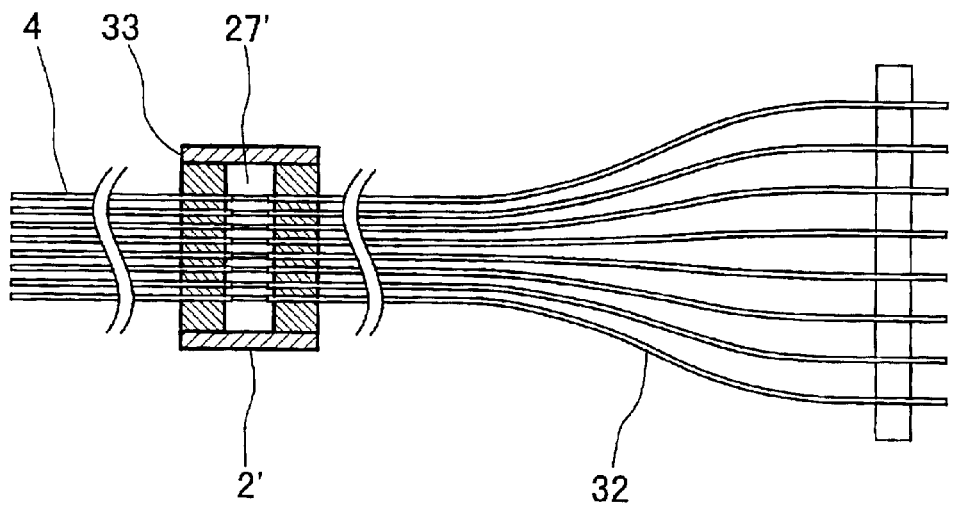
FIG. 13 is a schematic view of a multi-capillary array.
Figure 14:
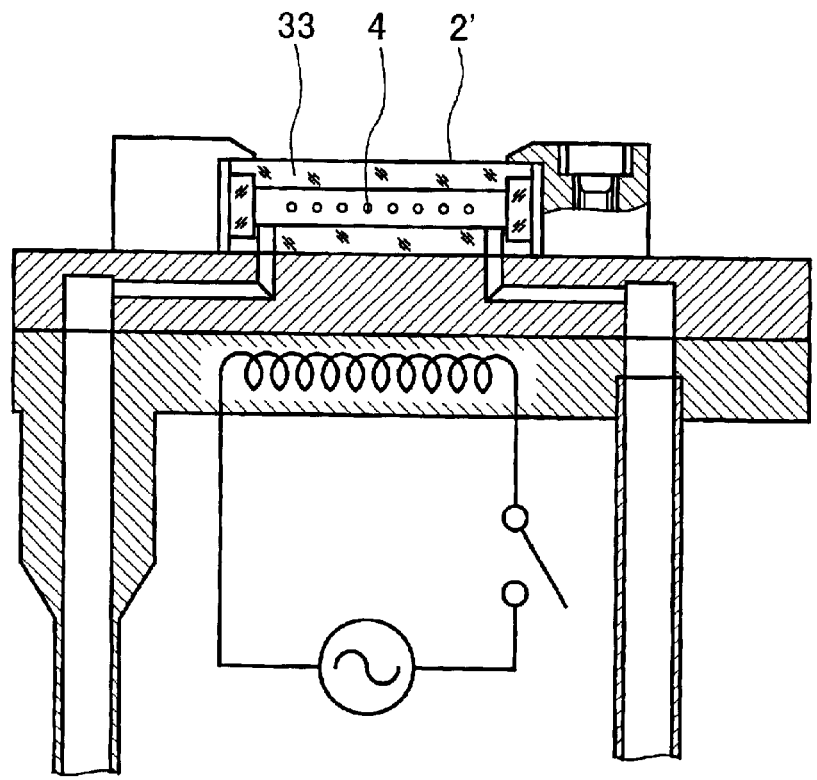
FIG. 14 is a cross-sectional view of the reaction chamber of the window-processing device for the coated multi-capillary array according to the present invention.
Figure 15:
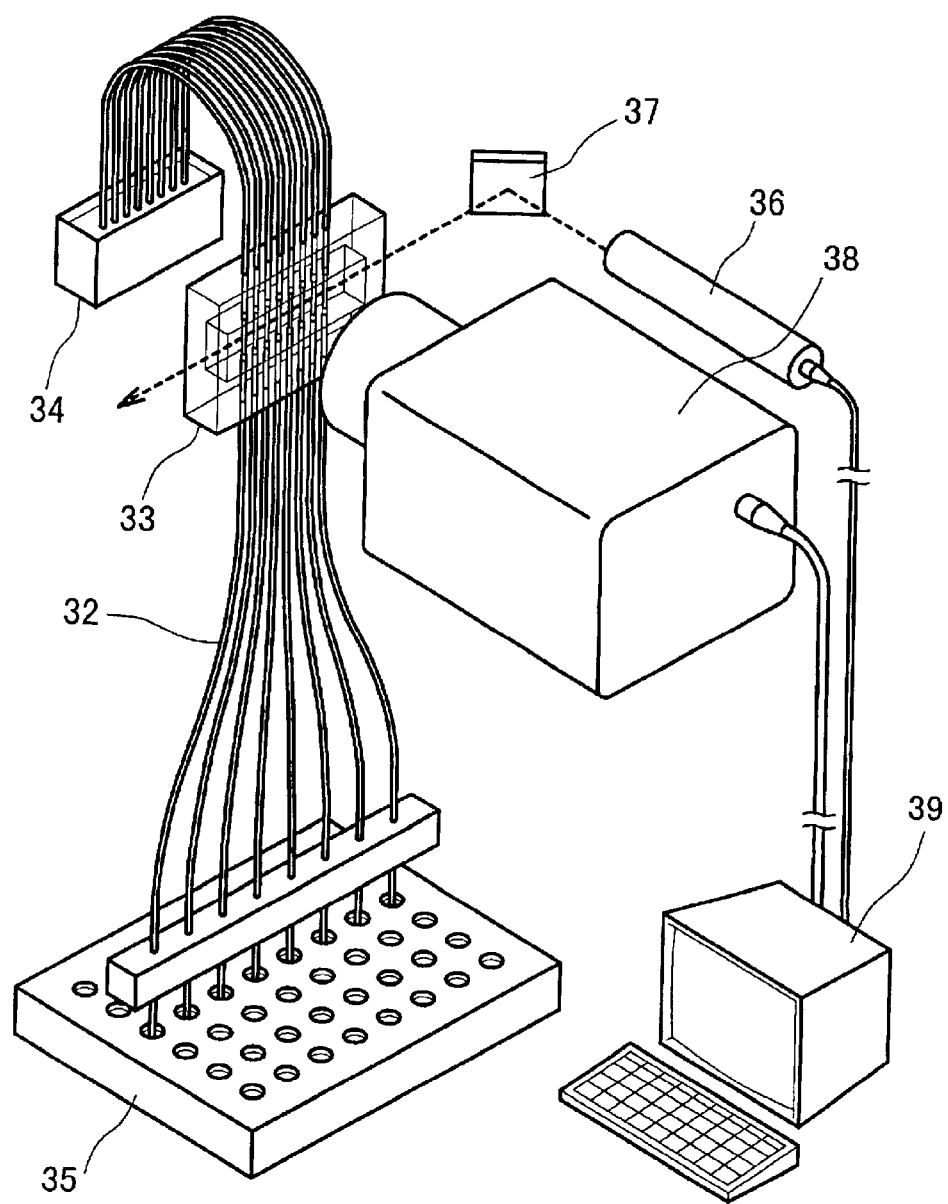
FIG. 15 is a schematic view showing a structure of an electrophoresis apparatus using the multi-capillary array of the invention.
Figure 16:
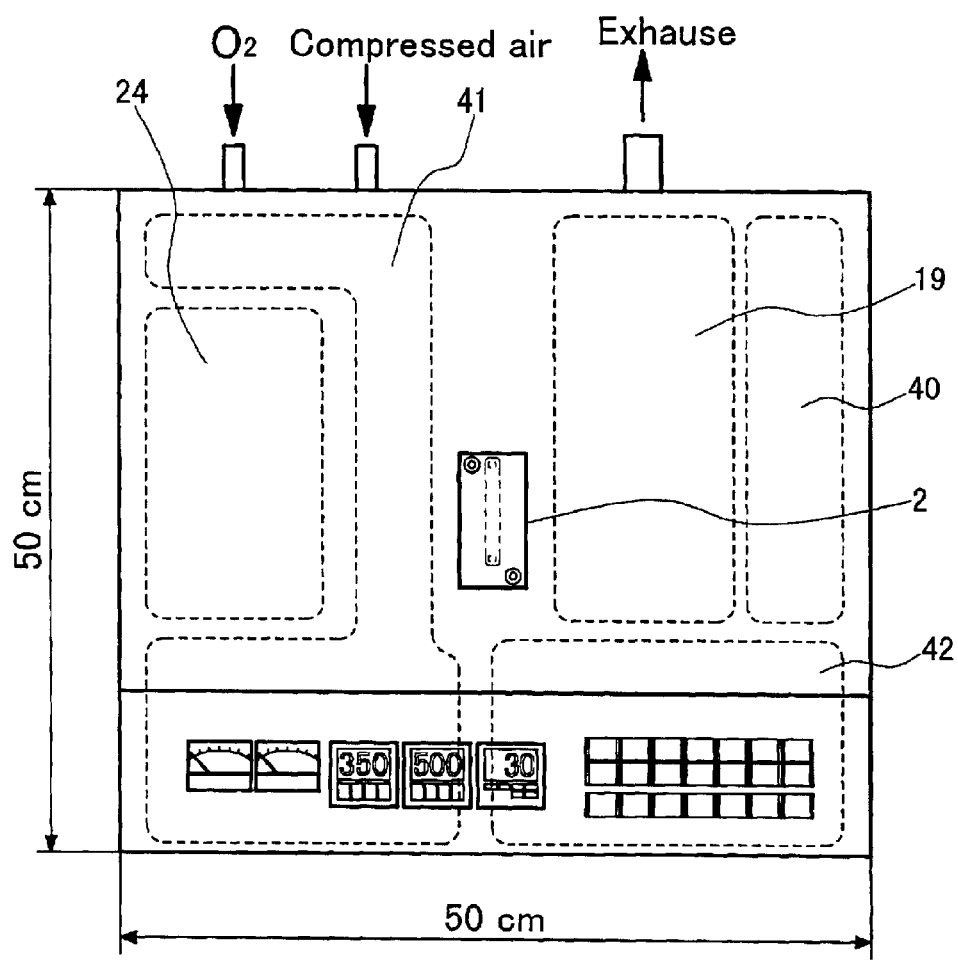
FIG. 16 is a plan view showing the window-processing device for coated capillary tubes according to the present invention.

FIGS. 1 to 16 are schematic views showing a device for processing a window for a coated-capillary tube according to the present invention. FIG. 1 is a perspective view showing a whole structure of the window-processing device for a coated-capillary tube according to the present invention, where a cover 3 on the upper surface of a main body 1 is opened and capillary tubes 4 are mounted in the reaction chamber. FIG. 2 is a plan view of FIG. 1 where the cover 3 is removed away. FIG. 3 is a perspective view showing a reaction chamber 2 and its periphery under the cover 3. FIG. 4 is a magnified perspective view showing a cross-section of a substrate 13, a lid 14 and a heating plate 17 shown in FIG. 3, where capillary tubes 4 are not set. FIG. 5 is a magnified perspective view similar to FIG. 4, where the capillary tubes 4 are set. FIG. 6 is a cross-sectional view and a schematic piping diagram of the reaction chamber 2. FIG. 7 is a flowchart showing operations after switching the power source on. FIG. 8 is a graph showing relationship between ozone concentrations and removal rates. FIG. 9 is a graph showing relationship between window-processing temperatures and removal rates. FIGS. 10A to 10C are magnified views of a capillary tube provided with a window, where FIG. 10A shows the window, FIG. 10B shows a profile of the edge of the window (part A) processed according to the present invention, and FIG. 10C shows a profile of the edge of the window (part A) processed according to a conventional technique. FIGS. 11A and 11B are graphs showing profiles of the edges of windows measured by a surface measuring instrument, where FIG. 11A shows the profile according to the present invention and FIG. 11B shows the profile according to the conventional technique. FIG. 12 is a magnified cross-sectional view of the reaction chamber 2 on the ozone supplying side. FIG. 13 is a schematic view of a multi-capillary array. FIG. 14 is a cross-sectional view of the reaction chamber 2 upon processing windows for the multi-capillary array. FIG. 15 is a schematic view showing a structure of an electrophoresis apparatus using the multi-capillary array. FIG. 16 is a plan view showing a structure inside FIG. 1.

[Embodiment 1]

With reference to FIGS. 1 and 2, the reaction chamber 2, the cover 3 for the reaction chamber 2, the capillary tubes 4, a stopper 5 and a scale 6 for determining the positions of the windows to be processed for the capillary tubes 4, a meter 7 for indicating a state of ozone generation, a temperature controller 8 for the reaction chamber 2, a temperature controller 9 for an ozone killer, a control switch 10 and a display unit 11 are arranged on the upper surface of the main body 1. As shown in FIG. 3, the reaction chamber 2 is provided with a substrate 13 having one or more grooves 12 for supporting the capillary tubes 4 and a lid 14 for holding the capillary tubes fit in the grooves 12. The reaction chamber 2 has a narrow space 15 generally at the center of the facing surfaces of the substrate 13 and the lid 14. When the lid 14 in FIG. 3 is removed, the grooves 12 for supporting the capillary tubes 4 will be exposed as shown in FIG. 4, into which the capillary tubes 4 are fit as shown in FIG. 5.

In order to process windows for the polymer-coated capillary tubes, first, the capillary tubes 4 are fit in the grooves 12 of the substrate 13 as shown in FIG. 4, and closed with the lid 14 which is then secured with a lid-securing screw 16. Then, as shown in FIG. 2, ends of the capillary tubes on one side are aligned against the stopper 5 anchored with respect to the scale 6 to determine the positions of the windows to be processed, thereby setting the capillary tubes 4. Since there are slight gaps between the grooves 12 and the respective capillary tubes 4, the capillary tubes 4 can move freely along the longitudinal direction for positioning. Once the capillary tubes 4 are set, the start switch 10 is pressed to initiate the device.

Hereinafter, operations following the initiation of the device will be described with reference to FIGS. 6 and 7.

First, a current is provided to a heater 18 inside the heating plate 17 beneath the reaction chamber 2 (S11). The temperature of the heating plate 17 is raised from room temperature to a temperature 20–30° C. higher than the temperature for processing windows (S12). When the temperature of the heating plate 17 reaches a temperature 20–30° C. lower than the window-processing temperature during the heating, a current is provided to a heater 20 of the ozone killer 19 (S13) to heat the ozone killer 19 to a temperature that allows the decomposition of excess ozone (S14). Once the temperature of the heating plate 17 reaches the temperature 20–30° C. higher than the window-processing temperature (S15), a electric valve 21 for compressed air opens so that compressed air is sent to an ejector pump 22 to generate a vacuum state (S16), while at the same time, a electric valve 23 for oxygen also opens to send oxygen to an ozone generator 24 (S17). Next, the power of the ozone generator 24 is switched on (S18) and the generated ozone is introduced from the supply port 25 of the reaction chamber 2, passes through the space 15, a discharge port 26 and the ozone killer 19, and is exhausted by the ejector pump 22. At this point, the window processing initiates and ends according to a timer (S19, S20).

The heat of the heating plate 17 heated to a temperature 20–30° C. higher than the window-processing temperature transfers to the capillary tubes 4 via the substrate 13 and the lid 14 forming the reaction chamber 2, thereby heating the capillary tubes 4 to the window-processing temperature. Ozone generated by the ozone generator 24 either makes contact with the heated capillary tubes 4 or is decomposed into $O_2$ and O radical as heated by an auxiliary ozone heater 28. Polymer coatings 4' of the capillary tubes 4 are gradually removed from the surfaces of the tubes 4 through an oxidative reaction with O radical. After about 20 minutes, the coatings 4' are completely removed, thereby providing windows.

Thereafter, the device performs a termination operation. Specifically, the device turns off the power of the ozone generator 24 (S21), closes the electric valve 23 for oxygen (S22), and halts a current supplied to the heater 18 inside the heating plate 17 (S23). Once the temperature of the heating plate 17 becomes sufficiently low (S24), the electric valve 21 for the compressed air is closed (S25).

FIG. 8 is a graph showing the relationship between ozone concentrations and removal rates obtained by a preliminary experiment using a polyimide coating formed on a Si wafer surface. The temperature of the Si wafer is about 250° C. As can be appreciated from FIG. 8, the higher the ozone concentration is, the faster the removal rate becomes. The removal rate at 5% concentration (by volume) is about 1.4 times faster than the removal rate at 2.5% concentration. Since the present embodiment aims at processing the windows within 30 minutes, the ozone generator employed in the present device is capable of generating ozone of a concentration of 0.5% or higher. Ozone has a risk of explosive decomposition and explodes at a concentration of around 10% at room temperature under atmospheric pressure. Therefore, it is necessary to provide the windows at a concentration of 10% or below.

In order to use ozone efficiently, preferably, the gap between the capillary tubes 4 and the space 15 where the ozone flows from the supply port 25 to the discharge port 26 is made narrow so that the ozone can efficiently make contact with the capillary tubes 4. If the gap is too narrow, the pressure loss will become large, requiring the ozone to be supplied under a higher pressure. This will be contrary to the feature and the aim of the present invention in that the ozone should be supplied to the space 15 inside the reaction chamber 2 under a pressure lower than atmospheric pressure to cause negative pressure to draw the ozone and prevent the ozone from leaking outside the device, thereby also serving as a seal. If the gap is too wide, more amount of ozone is required to flow a constant amount of ozone. Thus, according to the present invention, a set of replaceable members that are capable of adjusting the gap between the surfaces of the capillary tubes 4 and the inner wall of the space 15 in a range of 0.1 mm to 10 mm are replaceably used.

FIG. 9 is a graph showing the relationship between temperatures for processing the window (temperatures of the reaction chamber) and removal rates as the results of a preliminary experiment using a polyimide coating formed on a Si-wafer surface. The ozone concentration in this preliminary experiment is about 5%. The higher the window-processing temperature is, the faster the removal rate becomes. The removal rate at 300° C. is about 1.8 times faster than the removal rate at 250° C. When the window is processed at a temperature higher than 400° C., which exceeds the maximum working temperature of the polyimide, the coating region other than the window will be damaged. Accordingly, the temperature for processing the window must be lower than this temperature. Thus, the temperature appropriate for processing the window is considered to be in a range of 150° C. (preferably 200° C.) to 400° C. In the instant device, the window-processing temperature can be adjusted from room temperature to 400° C.

FIGS. 10A to 10C show magnified views of capillary tubes provided with windows. A window 27 in FIG. 10A is a part where a glass tube 4" is exposed by removing the polymer coating 4'. The polymer coating 4' is removed from the capillary tubes 4 where it is heated between the substrate 13 and the lid 14 of the reaction chamber 2 and where it makes contact with ozone, that is, where the surfaces of the capillary tubes 4 are exposed to the space 15 inside the reaction chamber 2. Parts of the capillary tubes 4 where they fit in the grooves 12 are heated but do not make contact with ozone since a slight amount of atmosphere is drawn in the gap between the grooves 12 and the capillary tubes 4 as the pressure of ozone supplied to the space 15 inside the reaction chamber 2 is made lower than atmospheric pressure. As a result, coatings on these parts are not removed. By the same mechanism, ozone is prevented from leaking to the atmosphere.

In the vicinity of the border of the capillary tubes where they fit in the grooves 12 and where they are exposed to the space 15 of the reaction chamber 2, the slight amount of atmosphere drawn in the gap between the grooves 12 and the capillary tubes 4 is mixed with ozone flowing inside the space 15. Accordingly, the ozone concentration becomes lower from parts of the capillary tubes 4 exposed to the space 15 toward the grooves 12. Since the rate of removing the coating is generally proportional to the ozone concentration, the border between the coating-removed window and the remaining coating (referred to as an "edge of window") can be a tapered coating 29 as shown in FIG. 10B, whose thickness around the periphery of the tube gradually becomes thinner toward the window. This shape of the window is a feature of the present invention which is distinctive from those produced by conventional techniques. According to conventional techniques, a window is produced by removing the coating generally perpendicular to the center axis of the capillary tube such that the thickness of the coating is constant as shown in FIG. 10C and the edge of the coating is uneven with carbonized portion 30 being produced. According to the present invention, the coating can be removed elegantly without producing any carbonized portion.

FIGS. 11A and 11B show profiles of the edges of the windows of the polymer-coated capillary tubes as measured by a surface measuring instrument. FIG. 11A shows the profile of the surface of the edge of the window formed according to the present invention, from which it can be appreciated that the thickness of the coating is gradually changing. According to the present invention, a slope of the surface of the coating is such that the surface makes an angle of generally 5 to 20 degrees with the center axis of the capillary tubes in the longitudinal direction, and a maximum of 70 degrees even when part of the coating is removed uneven in the peripheral direction of the capillary tube. On the other hand, referring to the surface profile of the edge of the window processed according to the conventional technique shown in FIG. 11B, the thickness of the coating is constant and generally perpendicular to the center axis of the capillary tubes in the longitudinal direction.

As can be appreciated from FIGS. 10B and 11A, the tapered coating 29 prevents stresses from concentrating on the glass tube 4" of the capillary tubes at the edge of the coating when the capillary tubes are bent after the windows are processed, thereby solving the problem of easy breakage caused by a concentration of stresses at the edge of the coating upon bending the capillary tube. In other words, the tapered coating serves like a cable holder for connectors or grommets used for electric wiring.

When the temperature of ozone supplied to the space 15 inside the reaction chamber 2 is lower than the temperature of the heated capillary tubes, the capillary tubes 4 will be cooled by the ozone, thereby suppressing the oxidative reaction. In order to pre-heat the ozone to a temperature generally equal to that of the capillary tubes 4 before applying ozone to the capillary tubes 4, the ozone pre-heater 28 is provided as shown in FIG. 6. The ozone pre-heater 28 may be omitted if an ozone pre-heating region 31 is provided by extending the distance between the ozone supply port 25 and the nearest capillary tube 4 as shown in FIG. 12 or if an ozone pre-heating region 31' is provided such that the heat of the heated plate 17 is transferred to a pipe extending from the ozone supply port 25 to the ozone generator 24.

In order to observe the removal of polymer coating 4' from the capillary tubes 4 and confirm the termination of the window processing, the lid 14 may be made of a light-transmitting heat-resistant material such as quartz glass. By making the lid 14 from quartz glass, the capillary tubes 4 can be heated by a lamp heater or a laser beam through the quartz glass. In addition, by radiating, through the light-transmitting glass, ultraviolet to the capillary tubes and the reactive gas filling the space inside the reaction chamber, ozone will absorb the ultraviolet (254 nm) to allow easy decomposition, by which windows can be made at a practically fast speed at a lower temperature (250° C. or lower).

[Embodiment 2]

One type of electrophoresis apparatuses using capillary tubes is an electrophoresis apparatus using a plurality of arrayed capillary tubes. The ends of the capillary tubes are aligned such that the windows are aligned in parallel to form a same plane. FIG. 13 shows an exemplary multi-capillary array. Windows 27' of the multi-capillary array 32 are covered and supported by a holder 33 to prevent the capillary tubes 4 from falling apart. According to the present embodiment, the holder 33 (made of non-polymer material in this case) is used as a reaction chamber 2' for processing the windows.

Specifically, instead of the substrate 13 and the lid 14 of the reaction chamber 2 shown in FIG. 6, the holder 33 shown in FIG. 13 is secured and used as the reaction chamber 2' as shown in FIG. 14. The multi-capillary array 32 is first assembled by using this holder 33, and then, the holder 33 is used as the reaction chamber to process the windows 27'. Therefore, capillary tubes without windows which are strong and handling-easy can be used to produce the multi-capillary array 32, thereby greatly enhancing the operation efficiency and allowing automation of producing a multi-capillary array that has conventionally been impossible. Similar to Embodiment 1, the capillary tubes may be supported by the holder with slight gaps provided therebetween.

[Embodiment 3]

FIG. 15 shows an exemplary electrophoresis apparatus using the multi-capillary array 32 of the invention shown in FIG. 13. The ends of the multi-capillary array 32 on one side are connected to a buffer bath 34 while the ends on the other side are connected to sample cells 35. A voltage is applied between the buffer bath 34 and the sample cells 35 to perform electrophoresis. A laser beam is radiated from a laser light source 36 to the holder 33 by using an optical system such as a reflection mirror 37 and the like to detect fluorescence from the windows 27' of the multi-capillary array 32 with a fluorescence detector 38. The obtained signal is processed and analyzed on a personal computer 39.

According to the method for processing a window of the invention, coating can be removed elegantly without applying heat or mechanical stresses to the glass tubes 4" and evenly-aligned windows can be formed without causing deformation such as bent of the capillary tubes. Accordingly, an electrophoresis measurement where all of the plurality of capillary tubes are transversely irradiated with a laser beam can be reliable.

In order to remove the polymer-coating 4' on the capillary tubes, a power source 40, a piping system 41, a controlling system 42 and the like are necessary other than the above-described reaction chamber 2, the above-described ozone generator 24 and the above-described ozone killer 19 for decomposing the remaining unreacted ozone. An arrangement of these constituent members according to the present invention is shown in FIG. 16. FIG. 16 is a schematic view showing an arrangement inside the device shown in FIG. 2 without the scale 6 and the stopper 5.

Referring to FIG. 16, the body of the device accommodates the ozone generator 24, the power source 40, the piping system 41, the ozone killer 19 and the controlling system 42 for controlling them. When the ozone generator 24 should generate ozone of a high concentration (0.5% or higher) required for the present invention, the size thereof as well as the corresponding ozone killer 19 will be as large as a conventional small-sized refrigerator. Although they can be connected with pipes to be used as the members of the window-processing device, they require a very large installation area. According to the present invention, the application of the device is specialized in processing a window for a capillary tube so that the ozone generator 24 and the ozone killer 19 are optimized and the entire constituent members can be accommodated in a small body of about 50 cm (width)×50 cm (depth)×30 cm (height), thereby producing a window-processing device for coated capillary tubes which can be used on a desk.

The present invention provides a small-sized device for processing a window for a coated capillary tube in a safe and inexpensive manner, where a polymer coating on the capillary tube can be removed for a selected target region, without affecting the glass tube as the base material of the capillary tube or requiring an after-treatment, any hazardous chemicals or a large-scaled device. This can contribute to mass production of capillary tubes and cost reduction thereof. Furthermore, since the coating can be removed clearly without applying heat or mechanical stresses on a glass tube, and no stresses is concentrated on the edge of the coating around the window, a strong and high-quality capillary tube, which does not shield or scatter light or cause background fluorescence by any residue, can be provided without unnecessarily weakening the strength of the capillary tube. Moreover, according to the present invention, a multi-capillary array with evenly-aligned windows can be produced without deformation such as bent. Accordingly, an electrophoresis measurement where all of the plurality of capillary tubes are transversely irradiated with a laser beam can be reliable. Since the windows can be processed after assembling the multi-capillary array, the operation efficiency can greatly be enhanced and automation of assembling a multi-capillary array can be realized, which has conventionally been difficult.

What is claimed is:

1. A method for removing a predetermined region of a coating of a polymer-coated glass capillary tube, comprising the steps of:

raising a temperature in a reaction chamber in which the predetermined region of the polymer-coated glass capillary tube is arranged; and reacting the predetermined region of the glass capillary tube with a reactive gas containing $O_3$ gas introduced into the reaction chamber so as to form the coating with a gradually decreasing thickness, the thickness decreasing in a certain area of the polymer coated glass capillary tube towards the predetermined region with the coating removed therein.

2. A method for removing predetermined regions of coatings of a plurality of polymer-coated glass capillary tubes, comprising the steps of:

raising a temperature in a reaction chamber, where the predetermined regions of the plurality of polymer-coated glass capillary tubes are arranged to form a plane and where the outer surfaces of the capillary tubes partially make gaps of 0.1 mm to 10 mm with the inner wall of the reaction chamber; and reacting the predetermined regions of the glass capillary tubes with a reactive gas containing $O_3$ gas introduced into the reaction chamber.

3. A method for removing a coating of a polymer-coated glass capillary tube according to claim 1, wherein the temperature in the reaction chamber is raised to 150° C. to 400° C., and the reactive gas containing $O_3$ gas having a concentration of 0.5% to 10% by volume is supplied to the reaction chamber where the pressure in the reaction chamber is smaller than atmospheric pressure.

4. A method for removing a coating of a polymer-coated glass capillary tube according to claim 1, wherein the temperature in the reaction chamber is raised to 100° C. to 400° C., the reactive gas containing $O_3$ gas having a concentration of 0.5% to 10% by volume is supplied to the reaction chamber where the pressure in the reaction chamber is smaller than atmospheric pressure, and ultraviolet rays are radiated to the reaction chamber.

5. A method for manufacturing a polymer-coated glass capillary tube having a predetermined region of a coating of the polymer coated glass capillary tube removed comprising steps of:

providing the polymer coated glass capillary tube;

raising a temperature in a reaction chamber in which the predetermined region of the polymer-coated glass capillary tube is arranged; and reacting the predetermined region of the glass capillary tube with a reactive gas containing $O_3$ gas introduced into the reaction chamber so as to form the coating with a gradually decreasing thickness, the thickness decreasing in a certain area of the polymer coated glass capillary tube towards the predetermined region with the coating removed therein.

6. A method for manufacturing a polymer-coated glass capillary tube according to claim 5, wherein the temperature in the reaction chamber is raised to 150° C. to 400° C., and the reactive gas containing $O_3$ gas having a concentration of 0.5% to 10% by volume is supplied to the reaction chamber where the pressure in the reaction chamber is smaller than atmospheric pressure.

7. A method for manufacturing a polymer coated glass capillary tube according to claim 5, wherein the temperature in the reaction chamber is raised to 100° C. to 400° C., the reactive gas containing $O_3$ gas having a concentration of 0.5% to 10% by volume is supplied to the reaction chamber where the pressure in the reaction chamber is smaller than atmospheric pressure, and ultraviolet rays are radiated to the reaction chamber.

8. A method for manufacturing a polymer-coated glass capillary tube according to claim 5, wherein a coating material is polyimide.

9. A method for manufacturing a polymer-coated glass capillary tube according to claim 5, wherein the reacting gas containing $O_3$ gas is an oxygen gas containing $O_3$ gas.

10. A method for manufacturing a polymer-coated glass capillary tube according to claim 5, wherein the polymer coated glass capillary tube is arranged perpendicular to a flow of reactive gas.

11. A method for manufacturing a polymer-coated glass capillary tube according to claim 5, wherein ultraviolet rays are radiated to the reaction chamber.

* * * * *